United States Patent [19]

Binner et al.

[11] Patent Number: 5,469,149
[45] Date of Patent: Nov. 21, 1995

[54] METHOD AND APPARATUS FOR PRODUCING A WOUND PACKAGE OF AN ENDLESS THERMOPLASTIC MATERIAL

[75] Inventors: Tobias Binner, Radevormwald; Klaus Schafer, Remscheid, both of Germany

[73] Assignee: Barmag AG, Remscheid, Germany

[21] Appl. No.: 93,764

[22] Filed: Jul. 19, 1993

[30] Foreign Application Priority Data

| Jul. 18, 1992 | [DE] | Germany | 42 23 751.3 |
| Sep. 5, 1992 | [DE] | Germany | 42 29 779.6 |
| Dec. 9, 1992 | [DE] | Germany | 42 41 343.5 |
| Mar. 2, 1993 | [DE] | Germany | 43 06 422.1 |
| Jun. 11, 1993 | [DE] | Germany | 43 19 312.9 |

[51] Int. Cl.$^6$ .................................................. G08B 21/00
[52] U.S. Cl. ............................ 34/677; 65/377; 65/332; 65/491; 65/492; 57/264
[58] Field of Search .................................. 340/670, 666, 340/673, 675, 676, 677; 264/103; 348/106; 356/238; 65/382, 377, 484, 492, 387, 491; 19/106; 68/13 R, 22 R; 28/100; 66/55, 104; 200/85 R; 57/264; 242/35.5 A, 178, 18 R; 8/151

[56] References Cited

U.S. PATENT DOCUMENTS

| 3,672,584 | 6/1972 | Macedo et al. | 242/18 R |
| 3,731,069 | 5/1973 | Goto et al. | 340/677 |
| 3,739,276 | 6/1973 | Dornberger | 340/677 |
| 4,007,457 | 2/1977 | Aeppli | 340/677 |
| 4,158,445 | 6/1979 | Newbegin | 242/178 |
| 4,720,702 | 1/1988 | Martens | 340/677 |
| 4,774,042 | 9/1988 | Schippers | 264/103 |
| 4,775,400 | 10/1988 | Wright et al. | 65/384 |
| 4,843,808 | 7/1989 | Rüge et al. | 57/264 |
| 4,956,902 | 9/1990 | Turek | 28/257 |
| 5,050,258 | 9/1991 | Fischer et al. | 8/151 |

Primary Examiner—Brent Swarthout
Assistant Examiner—Benjamin C. Lee
Attorney, Agent, or Firm—Bell, Seltzer, Park & Gibson

[57] ABSTRACT

A method and apparatus for continuously producing an endless thermoplastic material, such as yarn or tape, and winding the material into a package. A physical parameter of the package, such as its diameter or weight, is monitored, and a control signal is generated which is a function of the monitored physical parameter. The control signal is then compared to a predetermined reference signal, and an output signal is generated when the difference between the control signal and the reference signal exceeds a predetermined deviation. The output signal thus represents the quality of the material in the package, and it may be used to permit classification of the final product or to control the operating conditions of the apparatus so as to maintain a desired quality level.

31 Claims, 10 Drawing Sheets

METHOD AND APPARATUS FOR PRODUCING A WOUND PACKAGE OF AN ENDLESS THERMOPLASTIC MATERIAL

BACKGROUND OF THE INVENTION

The present invention relates to a method of producing and/or processing, as well as winding, an endless material of thermoplastic material, and more particularly, to a method of the kind referred to wherein signals are produced which are representative of the quality of the endless material.

In the context of texturizing yarn, such a method has been generally described in commonly assigned U.S. Pat. No. 4,720,702 to Martens, issued Jan. 19, 1988, (European Patent Specification 0 207 471). As disclosed in the prior patent, indications of the quality of the package or yarn produced are derived from quality parameters which do not relate directly to the actual measurements. This known method has been successfully applied in connection with yarns textured by a false twist texturing method.

Endless material, as understood herein, relates to yarns, ribbons, tapes, films, and foils. Endless materials of this kind are characterized in that they are produced by continuous operations or that they require continuous processing, with a plurality of packages being sequentially produced from the endless strand.

It is an object of the present invention to provide a method and apparatus of the described type, and more particularly a method and apparatus for winding smooth yarns, such as, in particular, yarns spun from fibers produced as endless synthetic filaments and wound up in spinning machines, with a value representative of the quality of the final product being continuously derived, and so as to permit classification of the final product and/or process control.

SUMMARY OF THE INVENTION

The above and other objects and advantages of the present invention are achieved in accordance with the present invention by the provision of a method and apparatus wherein a physical parameter of the package is measured, and the physical parameter or a value derived therefrom is compared against a predetermined representative value (desired value) or a tolerance range thereof, and an output signal is generated whenever the physical parameter or the value derived therefrom deviates from the desired value in an unacceptable manner. Thus the output signal is an unambiguous indicator of the quality of the endless material in the wound package.

The invention recognizes that the structure of the package onto which the yarn is wound, is significantly influenced by the quality of the produced yarn and that the condition of the package as defined by one or more of its parameters represents a reliable indication of yarn quality at any instant during the winding cycle (winding of the yarn to a package). As compared to methods heretofore employed, the special advantage resulting from the invention resides in the fact that any one of the parameters of the condition of the package is reflective, on the one hand, of the production process and of the actual state of the production and, on the other hand, also of the condition of the product. By monitoring any one or all of the parameters of the condition of the package and by its emission and evaluation as a quality signal a reliable indication of the condition of the process and of product quality may be obtained.

It has been found in particular that the manner in which the diameter develops over the entire winding cycle, or portions thereof, or the diameter of the package at defined instants of time, is representative of a great many quality parameters of the yarn and/or of the cross-wound package to be produced. Instead of using the diameter of package directly derived, indirect values may be drawn upon such as, for instance, the thickness of a layer formed on the package or bobbin in defined intervals, the increase in diameter (time derivative of the diameter), the diameter as a function of time, coefficients of the time function, and the like. It is of particular advantage to square the measured value (D) of the diameter and to form the first derivative of the squared value ($D^2$). The advantage resulting therefrom is, on the one hand, that as a result of the squaring operation irregularities in the progression appear correspondingly magnified and, on the other hand, that at a regular or constant progression the derivative of value ($D^2$) is a constant. Provided no irregularities occur, the derivative is proportional to the quantity of yarn wound in a given unit of time. By monitoring this derivative it is possible, therefore, also to monitor the orderly functioning of the yarn production by extruders, spinning pumps, spinning beams, and the like. A comparison with preestablished representative values and/or representative processes (desired values, desired ranges, desired processes) will be made in any event. Such desired values are preestablished in respect of qualitatively acceptable yarns or cross-wound packages. As stated above, tolerance ranges may be set around such preestablished representative values, so that quality signals will be released only upon deviation from the tolerance range. The quality signal may be released also, however, in case of any deviation from an exact match between the measured diameter of the package, or the value derived therefrom, and the corresponding representative value.

In a particularly advantageous embodiment as applied to a multi-station textile machine, the conditional parameter of each package at every winding position is measured, a mean value is formed from the measured conditional parameter of every package or from a value derived therefrom, the conditional parameter or the value derived therefrom is compared continuously or at predetermined instants of time with the mean value or a tolerance band related thereto, and the quality signal is released in case of a deviation.

Mean value as used herein is understood not to connote mean value in a strict mathematical sense. For practical purposes, the mean value is formed by feeding the conditional parameter or the value derived therefrom to a filter of a predetermined time constant. The selection of the time constant is determinative of the number of measured values to which the mean value relates. However, other electronic components are also available for the forming of mean values, such as, for example, low-pass filters.

In the production and/or processing of yarns made from thermoplastic materials, specific problems arise as a result of very high winding speeds. In texturing machines these are above 1,000 m/min, and in spinning machines they are above 3,000 m/min. The mensural problem of finding the diameter, at a constant surface speed of the takeup package is avoided by a process which involves measuring the surface speed and the rotational speed of the package and, in the case of films and foils, by a process wherein the thickness of the film or foil is measured. An additional or alternative indication may be obtained by a method wherein the measured physical parameter is the quantity or weight of the liquid finish which adheres to the yarn and the package. The quantity or weight of the liquid finish may be measured by measuring the throughput weight of the thermoplastic material per unit of time and the increase in the weight of the package per unit of time, and this may be done without the necessity of contacting the endless material.

A further physical parameter which may be measured is the density of the package. The density, as defined herein, is the quotient of the measured weight and the measured package diameter. This quotient, at a uniform length of the package remaining the same throughout the winding cycle, is a measure of the distribution of the mass of the yarn over the diameter of the package.

As stated hereinabove, endless materials made from thermoplastic material must be manufactured and/or processed at a constant speed. Not only does this refer to the linear speed of the material, but to the quantity produced per unit time as well, which also must stay constant. To carry out such measurements is obviously difficult, and the problem may be solved by continuously measuring the weight of the package and monitoring the change in its weight during a winding cycle. One example of a method of measuring the weight involves the monitoring of the deflection of the spindle or spindle bearing caused by the weight of the package.

Another suitable measuring method for determining the weight of the package involves the use of a winding head having a frame structure which mounts the package supporting spindle and which is mounted for pivotal movement about a transverse axis. It is thus possible to determine the weight of the package from the torque exerted by the frame structure and which results from the weight of the package.

The above method may be particularly useful in cases where a direct measurement of the deformation of a spindle or of its bearing are so critical that other disturbances, such as oscillations, are superimposed on the weight-induced deformation and lead to distorted measurements.

The quality signal may be released as an alarm signal and/or may be used as an indication of the quality of the produced package and/or may be used as a process control signal. As an alarm signal, the signal may be released optically or acoustically, or it may be released as a continuous graph. It may also be utilized, however, as a qualitative indicator of the produced package, by separating the actual measurement data, or comparative data derived therefrom, and the representative values into classes of quality and by assigning them as a mark of quality to the manufactured goods, by means of a machine-integrated computer. As a process control signal, the quality signal may also serve to turn off the machine or to control the yarn delivery speed, the yarn takeup speed, the spinning speed, and/or other process parameters suitable to correct those quality parameters which often lead to deviations of the determined package diameter or the value derived therefrom, from the corresponding representative value. The disclosed methods of utilizing the signal are characterized by an effective and, at the same time, sensitive way of influencing the process, product, and quality during ongoing process and production. As previously indicated, the process control of the present invention is of advantage in that it permits immediate and instantaneous correction of products and/or processes in progress. In the past, such control had to be performed manually; direct intervention in the process was not possible. Until such manual control was performed, inferior production was, in the meantime, unavoidable.

It is also possible to measure continuously several package parameters and to control different process parameters on the basis of each of the conditional parameters. An advantageous further alternative resides in classifying the measured conditional parameter or its deviation from a desired value and in controlling several process parameters on the basis of such classification. For instance, during production of a yarn, the rotations of a pump may be adjusted in cases of large deviations in yarn thickness, or the withdrawal speed or draw ratio may be changed in case of deviations below a certain limit.

In multi-position textile machines, the positions may be compared, and signals may be generated in case of deviations from a predetermined mean value or a predetermined tolerance range relative to the mean value. If the majority of the takeup positions do not synchronously perform the winding operation, a correction will be necessary regarding the different starting times of their winding cycles, since to compare the diameters is useful only when the comparison occurs at identical instants of the winding cycle, i.e., for example, at a certain time interval after the start of the winding cycle.

To carry out the method of the present invention, it is necessary to solve the further problem of making available a takeup machine which cooperates with sensors which detect the selected conditional parameter of the packages. Where the weight of the package is to be determined, the frame structure of the winding head is supported substantially along the line of its center of gravity and, more particularly, is pivotably mounted, so that the weight of the winding head itself is balanced and does not influence the measured value determination of the package weight. In this sensor winding head, the measuring device is arranged preferably stationarily, and the action of force from a torque of the winding shaft with respect to the suspension of the winding head is measured continuously.

Such sensor winding heads may be used in spinning systems and in a slit-film production line, in each of which production and quality as well as process control are continuous monitored for optimizing the product quality.

BRIEF DESCRIPTION OF THE DRAWINGS

FIG. 2A illustrates the yarn traversing mechanism of FIG. 1A with an arrangement of the measuring roll for determining the package weight;

BRIEF DESCRIPTION OF THE PREFERRED EMBODIMENTS

Illustrated in the Figures are several embodiments which relate to the spinning of continuous filament yarns. The following description of the spinning installation applies to all Figures. Special characteristics of the present invention, as they result from the individual embodiments, are then described separately.

A continuous filament yarn 1 is spun from a thermoplastic material. The thermoplastic material is supplied via a hopper 2 to an extruder 3. The latter is driven by a motor 4 which is controlled by a motor control 49. In extruder 3, the thermoplastic material is melted. This is achieved in part by the deformation process (shearing energy) to which the material is subjected by the extruder. In addition, a heating system 5, for example, in form of a resistance heater, is provided which is controlled by a thermal control 50. Through a melt line 6 which accommodates a pressure sensor 7 for measuring the melt pressure for a pressure-speed control of the extruder, the melt advances to a gear pump 9 which is driven by a pump motor 44. The pump motor is controlled by a pump control 45 such that the pump speed is finely adjustable. The pump 9 delivers the melt flow to a heated spin pack 10, the underside of which accommodates a spinneret 11. From the latter, the melt exits in form of strands 12 of fine filaments. The strands of filaments advance through a cooling shaft 14. In the latter an air current 15 is directed by blowing transversely or radially to the web of filaments 12, thereby cooling the filaments.

At the end of cooling shaft 14, the web of filaments is combined to a yarn 1 by a spin finish application roll 13 and provided with a liquid spin finish. A delivery roll or godet 16 withdraws the yarn from cooling shaft 14 and spinneret 11. The yarn loops several times about godet 16. To this end a freely rotatable guide roll 17 in a crossed arrangement relative to godet 16 is used. The godet 16 is driven at a preadjustable speed by a motor 18 and frequency transmitter 22. The withdrawal speed is by a multiple higher than the natural speed of exit of filaments 12 from spinneret 11.

Arranged downstream of godet 16 is a further draw roll or godet 19 with a further guide roll 20. Both correspond in their arrangement to delivery roll 16 with guide roll 17. For the drive of draw roll 19 a motor 21 with a frequency transmitter 23 is used. The input frequency of frequency converters 22 and 23 is uniformly preset by a controllable frequency transmitter 24. In this manner, it is possible to adjust individually the speed of delivery roll 16 or draw roll 19 on frequency converters 22 and 23. The speed level of draw roll 16 and draw roll 19, however, is collectively adjusted on frequency converter 24.

Figure 1:
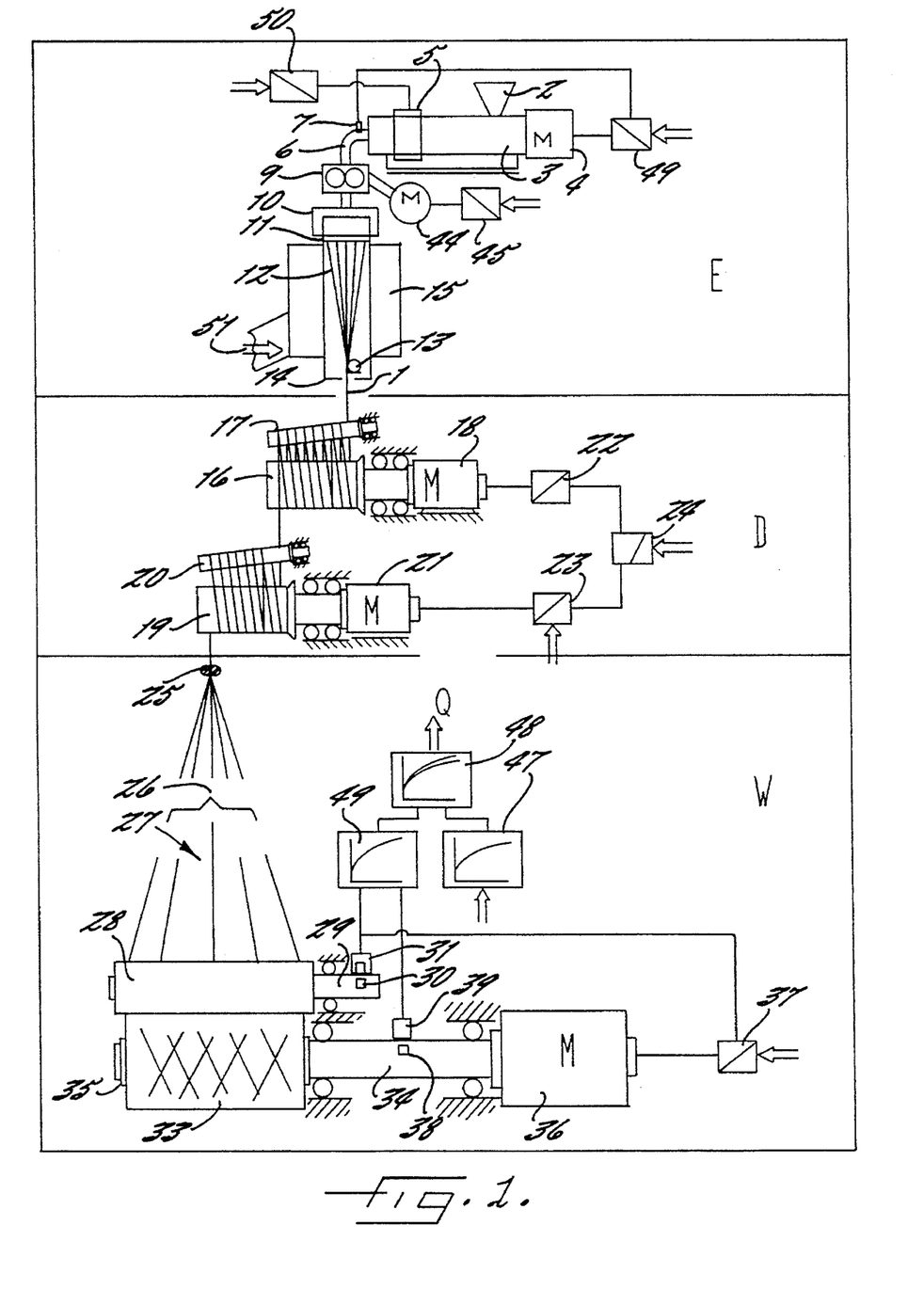
FIG. 1 is a schematic view of an apparatus for spinning continuous filament yarns, and which embodies the features of the present invention.
Figure 1A:
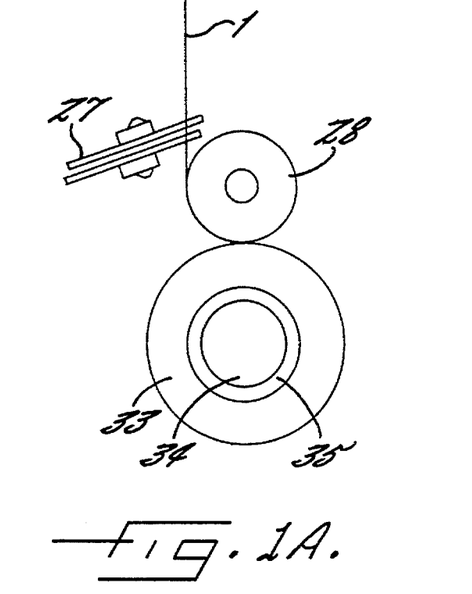
FIG. 1A illustrates a yarn traversing mechanism with oppositely rotating blades and a measuring roll arranged on the package for determining the package diameter.
Figure 1B:
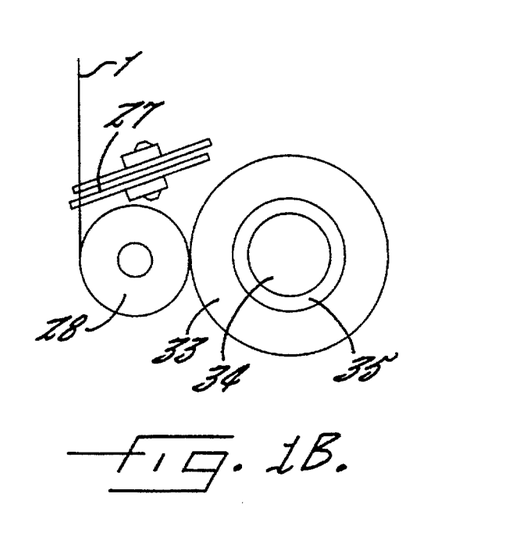

From draw roll 19, yarn 1 advances to a so-called "apex yarn guide" 25 and thence into a traversing triangle 26. In FIG. 1, a yarn traversing mechanism 27 in accordance with the illustration of FIG. 1A is shown. This traversing mechanism employs oppositely rotating blades which traverse yarn 1 over the length of a package 33. In so doing, the yarn loops, downstream of traversing mechanism 27, about a contact roll 28. The contact roll rests against the surface of package 33, and serves to measure the surface speed of package 33. The package 33 is formed on a tube 35 secured on a winding spindle 34. Winding spindle 34 is driven by a spindle motor 36 and spindle control 37 such that the surface speed of package 33 remains constant. To this end, the speed of contact roll 28 freely rotatable about a shaft 29 is scanned as a controlled value by means of a ferromagnetic insert 30 and a magnetic pulse generator 31.

It should be noted that yarn traversing mechanism 27 may also be a standard cross-spiralled roll with a yarn guide traversing in a cross-spiralled groove over the range of traverse.

In FIG. 1, the diameter of package 33 is continuously measured as a physical parameter, or a value derived from the diameter may be measured. Likewise, the weight may be considered as such a value, which is however accompanied by factors of interference, such as density of the wound package, entrapped air, crossing angle, and others. Therefore, it is not possible to consider the determined weight as an absolute value but only as a measured value which can be compared with a reference value. To determine the diameter, the speed of spindle 34 and the speed of contact roll 28 lying against the surface of the package are measured. To this end use is made of ferromagnetic inserts 30 and 38 in spindle 34 and contact roll 28, respectively, as well as corresponding pulse generators 31, 39. While the speed of contact roll 28 is simultaneously supplied as controlled value for the adjustment of spindle motor 36 via spindle control 37, the speed of spindle 34 is also used to control yarn traversing mechanism 27, which is not described in further detail. In addition however, both signals are converted into diameter D in a computer unit 46. In a preferred embodiment, a multiplier stage may be provided for continuously forming the square of the diameter. Thereafter, the first derivative of the square is formed. As may be seen from FIG. 9, the first derivative of the value $[d(D^2)]$ theoretically has to be a constant. For this first derivative is proportional to the quantity of furnished yarn. But ideally the quantity of yarn produced per unit time in the production of synthetic filaments is absolutely constant.

Figure 9:
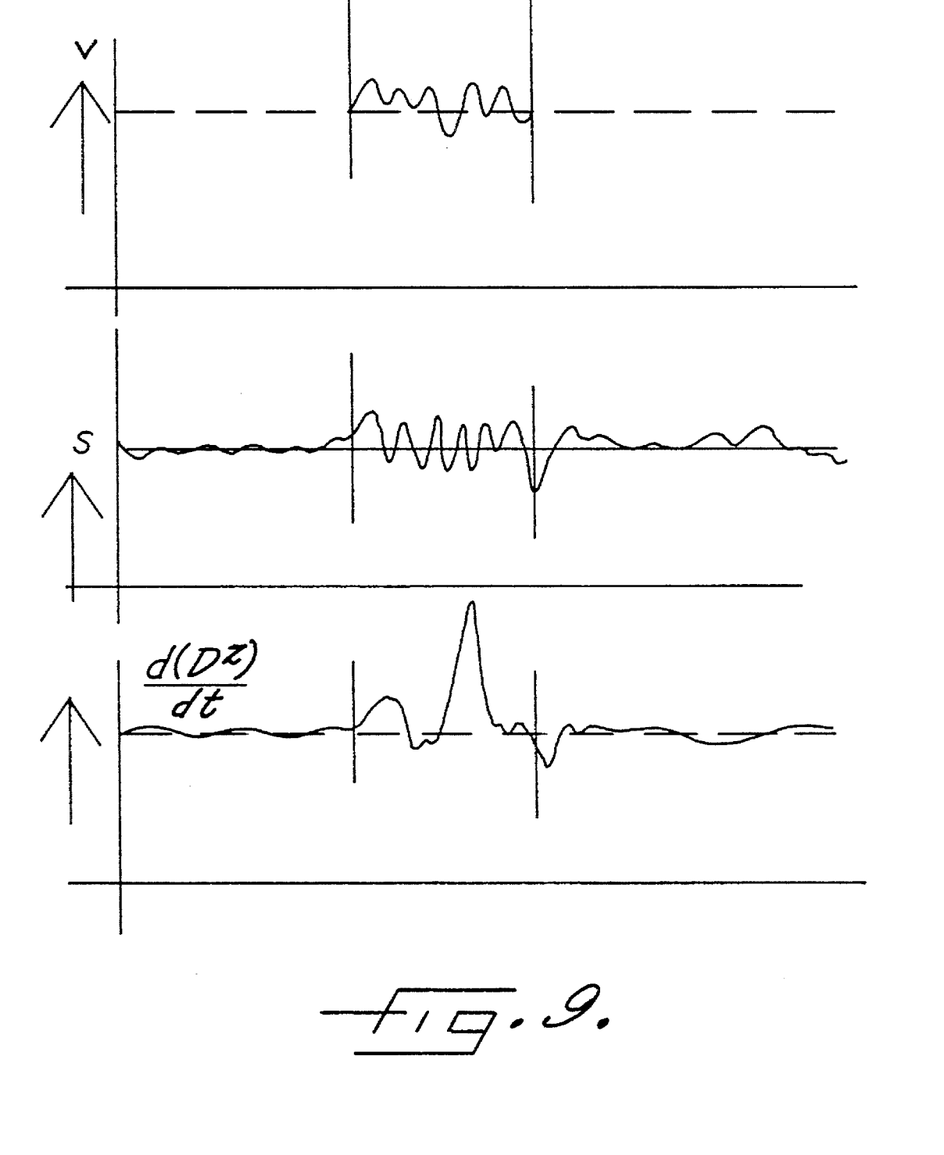
FIG. 9 is a diagram of yarn winding speed, yarn tension, and the derivative of the package diameter, developed over a predetermined time interval.

FIG. 9 depicts a diagram of yarn tension as a function of time. A disturbance in the tension s of the yarn was deliberately introduced into the thread tension graph, by interference with the winding speed v. In parallel thereto, the first derivative of value $(D^2)$ was continuously recorded. As may be seen, as deviations in thread tension occurred, the continuity of the first derivative was disturbed in a noticeable fashion. By coordinating the deviations in thread tension s and deviations in the first derivative $D^2$, certain errors in the production process may be determined.

As shown in FIG. 1, the signal representative of the diameter or the signal derived therefrom, as described above, is then supplied simultaneously with a previously stored reference signal from memory 47 to a comparison unit 48. The difference signal of comparison unit 48 will then serve as output signal for quality Q.

Figure 2:
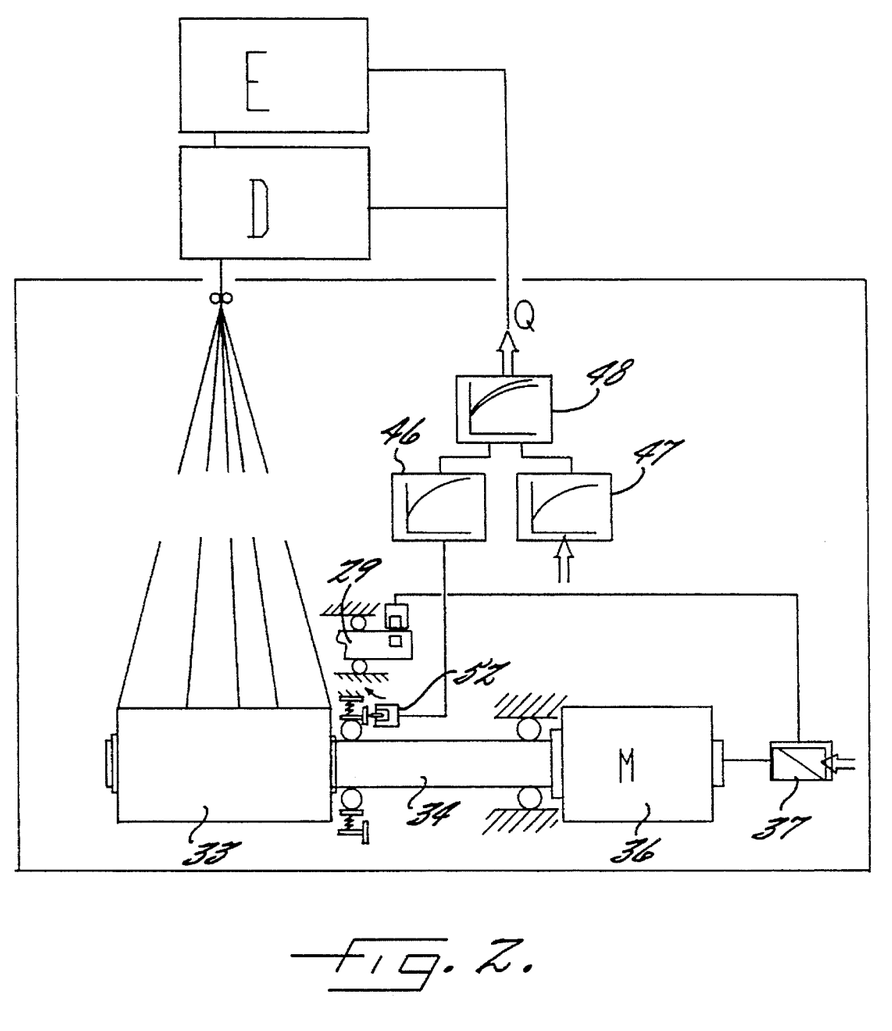
FIG. 2 illustrates the takeup portion of the spinning system of FIG. 1 with means for determining the package weight.

In the embodiment of FIG. 2, the weight of package 33 is determined. For this reason, spindle 34 is resiliently mounted in a bearing. The spring-elastic deflection of the bearing is measured. To this end a weight sensor 52 is shown. In practice, the latter includes strain gauges which are arranged on such bearing parts which are deformable as a function of the weight of the package. The course of the weight is compared with a desired value course stored in memory 47. In a comparison unit 48, the difference value is formed and the quality signal Q is derived therefrom. The quality signal again can be used to influence one or several process parameters in the extrusion (box E in FIG. 1), or the drawing (box D in FIG. 1), or even the spindle control 37.

FIG. 2A shows a modified arrangement of winding spindle 34 and contact roll 28, which is preferred when determining the package weight and its change during the winding cycle. In this embodiment, an action of force of contact roll 28 superimposing and possibly falsifying the package weight is compensated in that contact roll 28 is pressed laterally against the surface of package 33.

Figure 3:
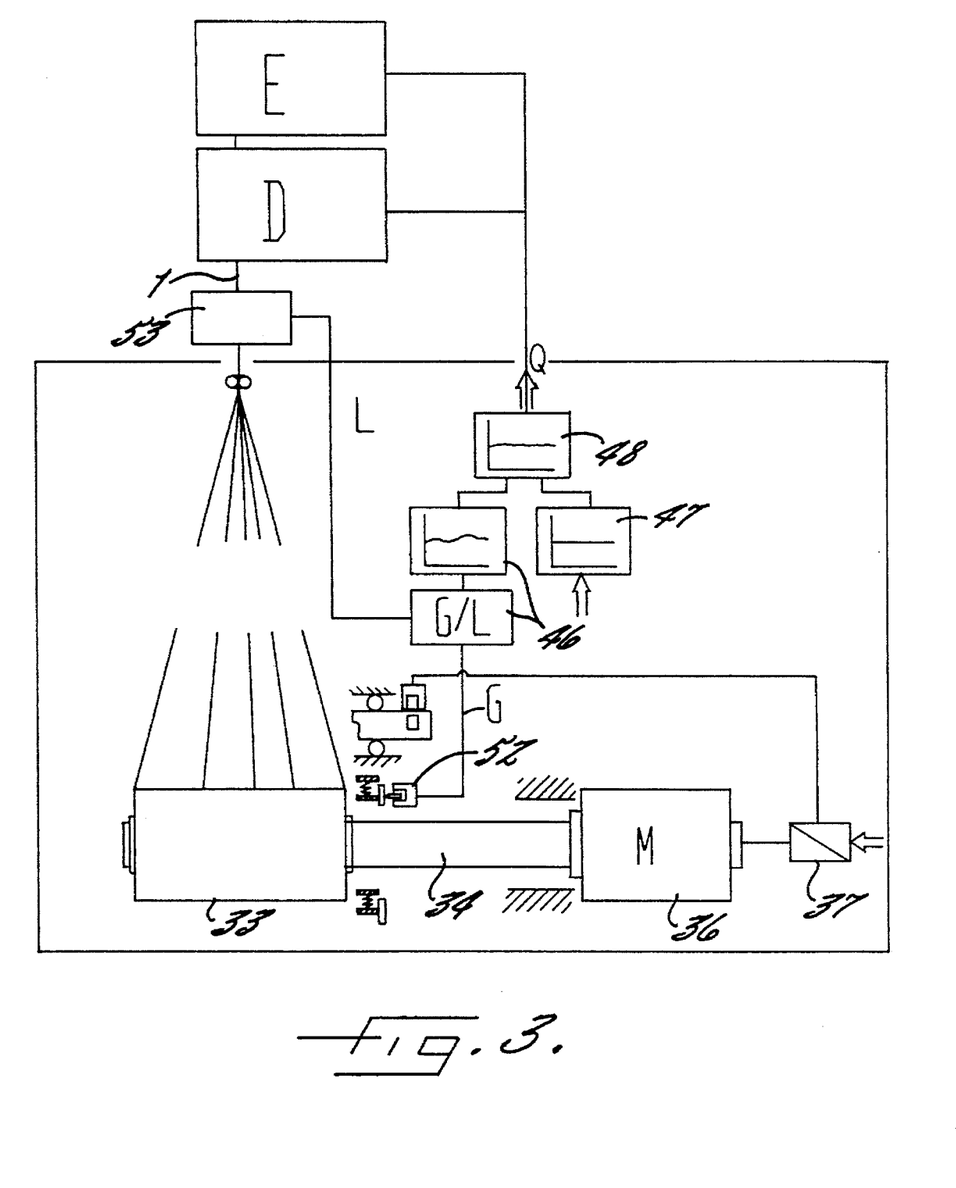
FIG. 3 shows the arrangement of FIG. 2 with provision for additionally determining and processing a signal indicating the length of the advancing yarn.

In the embodiment of FIG. 3, the denier of yarn 1 on package 33 is continuously measured. To this end, the package weight G is continuously measured on the one hand, as to which reference may be made to FIG. 2. In addition, the length L of the yarn advancing to package 33 is measured by a linear measuring device 53. The quotient of weight G and length L of the yarn wound on the package results in the denier. The generated output signal Q, as described above, is further processed.

To this end, the actual value from computer 46 is again compared in comparison unit 48 with the desired value input in memory 47.

Figure 4:
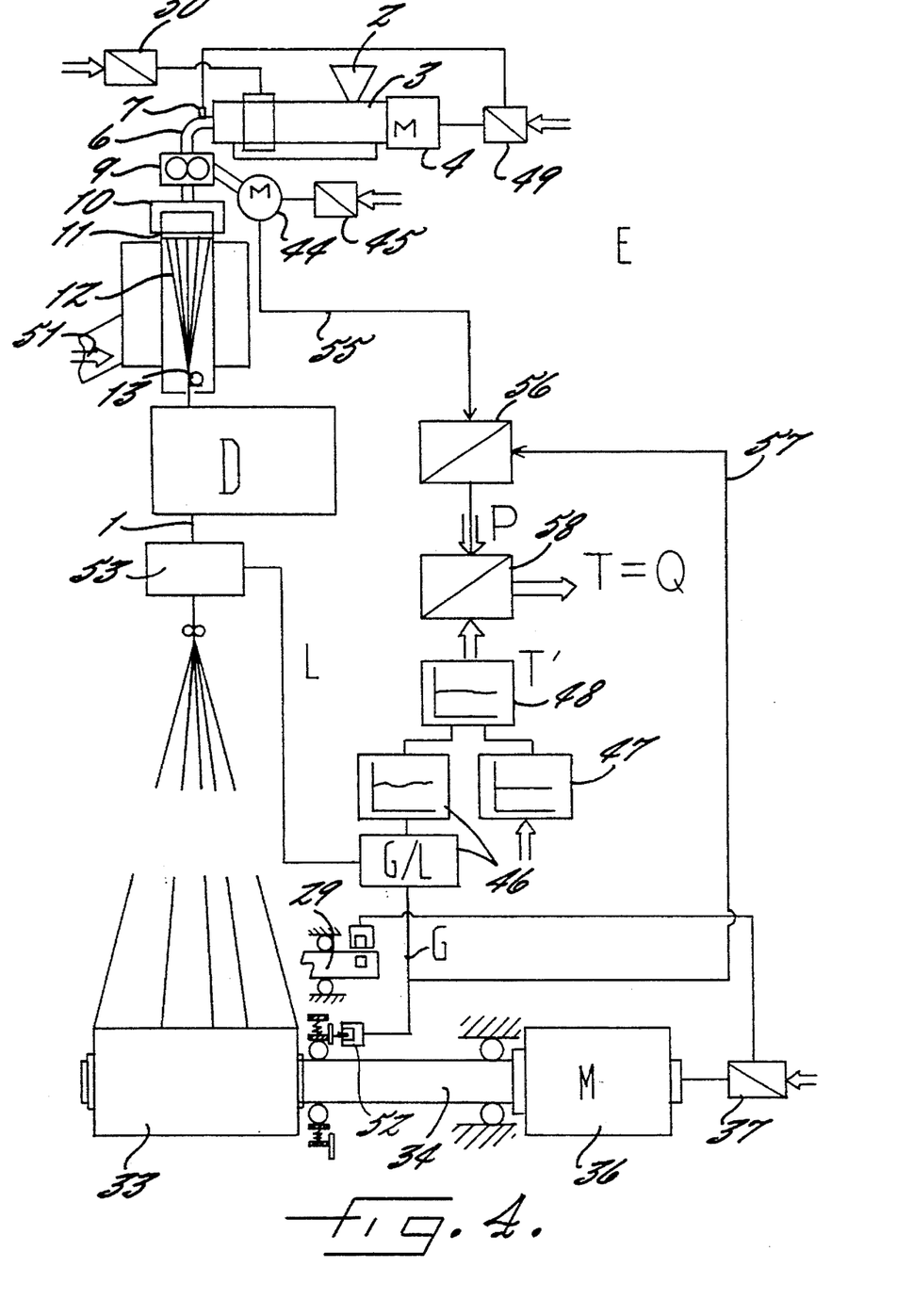
FIG. 4 shows a spinning system of FIGS. 1 and 3 with provision for additionally determining and processing a signal indicating the yarn denier.

Illustrated in FIG. 4 is that the denier measurement is corrected in addition by determining the applied spin finish. Spin finish application is here described as the quantity of liquid applied to the yarn. To perform this application, a device 13 (spin finish applicator) is used which is arranged in cooling shaft 14. To determine the application of the spin finish, the motor 44 of metering pump 9 is provided with a speed sensor not shown. Since the pump is a metering pump in which the discharge is highly speed-dependent, output signal 55 represents the throughput very accurately. Output signal 55 (throughput signal) is supplied to a computer component 56. The latter also receives in addition via a weight signal 57 the weight G which is determined by weight sensor 52. The difference between the weight determined by weight sensor 52 and the throughput determined by signal 55 integrated over the time results in the actual weight of the spin finish application P. The latter as applied per unit time results likewise from the difference of the weight measured per unit time and the time-dependent throughput.

In component 58, the spin finish application P is used to correct the denier value T' as is determined by the arrangement of FIG. 3. Insofar reference may be made to the description of FIG. 3. The output signal of computer component 58 represents then the real denier, namely either the mean value when measured integrated over the time, or the instantaneous value when the respective measurements occur per unit time. This denier T again can be used as quality signal Q.

Figure 5:
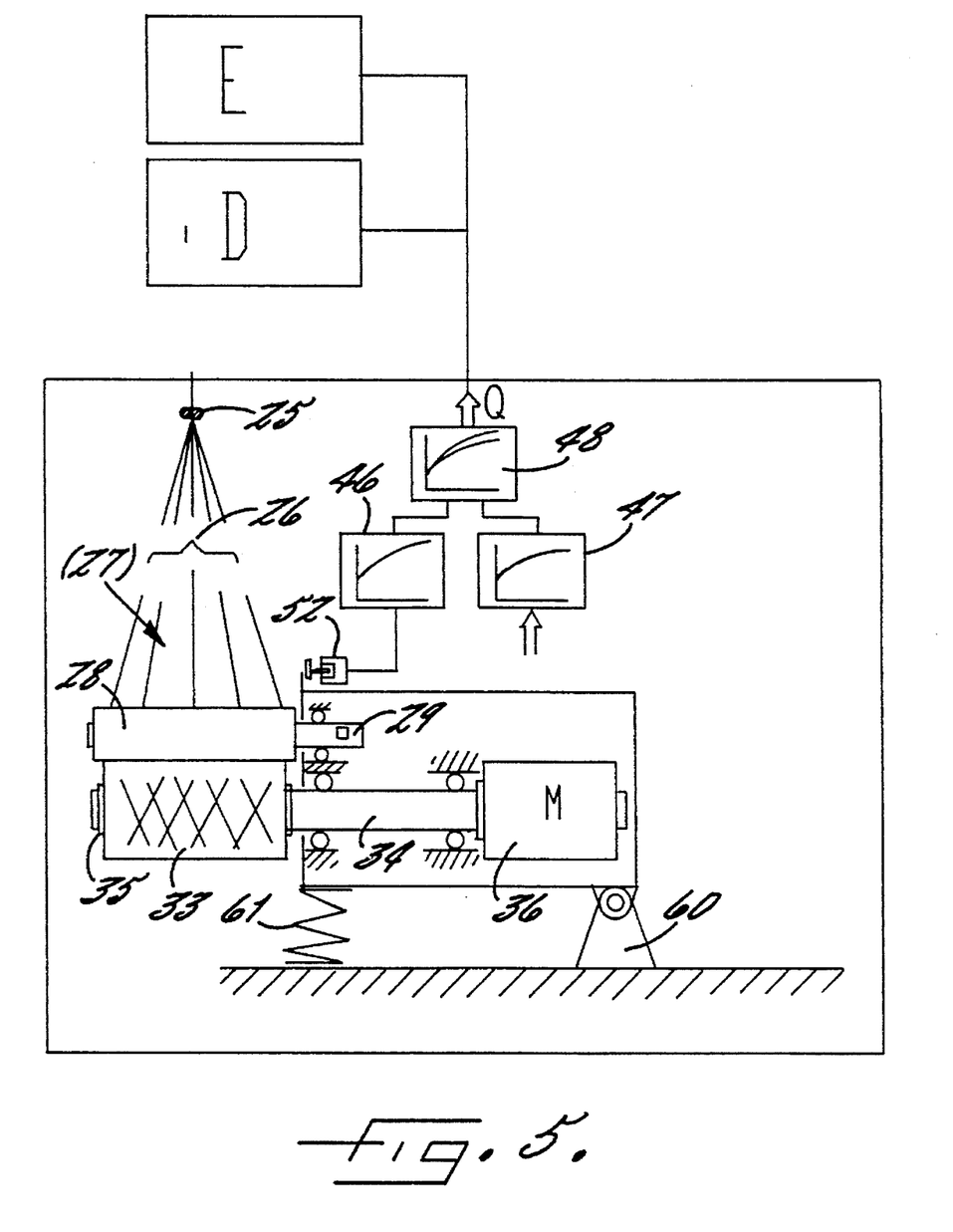
FIG. 5 shows the takeup portion of the spinning apparatus with a winding head sensor for determining the change in weight of the package during the winding cycle.

In the embodiment of FIG. 5, the weight of packages 33 is determined in that the entire takeup machine, hereafter winding head, is mounted in a spring suspension. To this end, on the side facing away from spindle 34 the winding head is mounted for pivotal movement in a swing support 60, with the pivoting plane extending substantially vertically. On the other side which faces spindle 34 and package 33, the winding head is supported in a spring 61. The latter is sufficiently strong, so that the weight increase of package 33 effects only a slight deflection which has no effect on the yarn path geometry.

The deflection of the winding head is picked up by a measuring device 52 and supplied via computer unit 46 and desired value memory 47 to comparison unit 48. This comparison unit generates the quality signal Q. The quality signal again can be used to influence one or several process parameters in the extrusion (box E of FIG. 1), or the drawing (box D of FIG. 1), or even the spindle control.

The quality signals Q which have been generated, as previously described, by the takeup device, are further processed as follows: the quality signal Q may be output as optical or acoustic alarm or as a graphic record. The latter allows to mark and classify the produced package 33.

Alternatively or additionally, the quality signal Q may then be supplied to one or several of the control means 23 for draw roll 19 to influence the drawing; to 24 to control the withdrawal speed;

45 to control the pump speed;

49 to control the extruder speed;

50 to control the heater; or 51 to control the cooling device.

The extruder control 49 is activated in particular when no metering pump 9 is used. In this instance, the extruder 3 functions as a pump and the activation of extruder control 49, i.e., the rotational speed control of the extruder, allows to influence the output of extruder 3.

When a metering pump 9 is used, the throughput quantity may be influenced by spin pack 10 and spinneret 11 by activation of pump control 45, i.e., the rotational speed control of metering pump 9.

The activation of cooling air control 51 allows to influence cooling. This has an effect on the yarn denier T. In particular, it is also possible to influence the uniformity of the individual filaments with the use of special cooling devices which allow to cool the webs of filaments 12 and/or spinneret 11 in sectors.

In the embodiment of FIG. 1 all parts of the system which are necessary to produce yarn 1, i.e., to extrude the thermoplastic material, are combined in a box indicated at "E". The individual parts of the system are possibly exchangeable. Accordingly in this event other parameters are controlled. In particular, it is possible to replace extruder 3 with a discharge pump, and likewise various other possibilities of cooling the filament web are given.

Shown in the embodiment of FIG. 1 is that the produced yarn 1 is drawn by godets 16 and 19. All elements which in the embodiment are used for drawing, are combined in the box indicated at "D". In the present high-speed spinning process, drawing by godets may also be eliminated. In this instance, the yarn 1 is withdrawn from spinneret 11 either by a single godet and advanced to the winding head, or it is withdrawn directly from the spinneret by the takeup device. On the other hand, drawing may also occur by further methods, so that in this instance, block "D" would have to be replaced or supplemented with further elements, for example, an additional godet, a heater, in particular a heating tube.

In the illustrated embodiment, the quality parameter Q may be used to activate frequency converter 24 to control delivery and/or frequency converter 23 to control the draw ratio.

The activation of frequency converter 24 allows to influence the speed of godet 16 and godet 19 without changing the speed ratio. In this instance, the draw ratio remains constant, whereas the yarn speed changes. As a result, the denier T can be influenced.

The activation of frequency converter 23 allows to influence the speed ratio between godets 16 and 19, and to thus change the draw ratio. The change of the draw ratio allows to vary the strength conditions of the yarn, but also the denier.

Finally, the spindle control allows to also control by means of quality parameter Q the circumferential speed of package 33 which is regulated by contact roll 28. This results in particular in an influence on the package buildup and the yarn tension under which the yarn is wound on the package.

Figure 6:
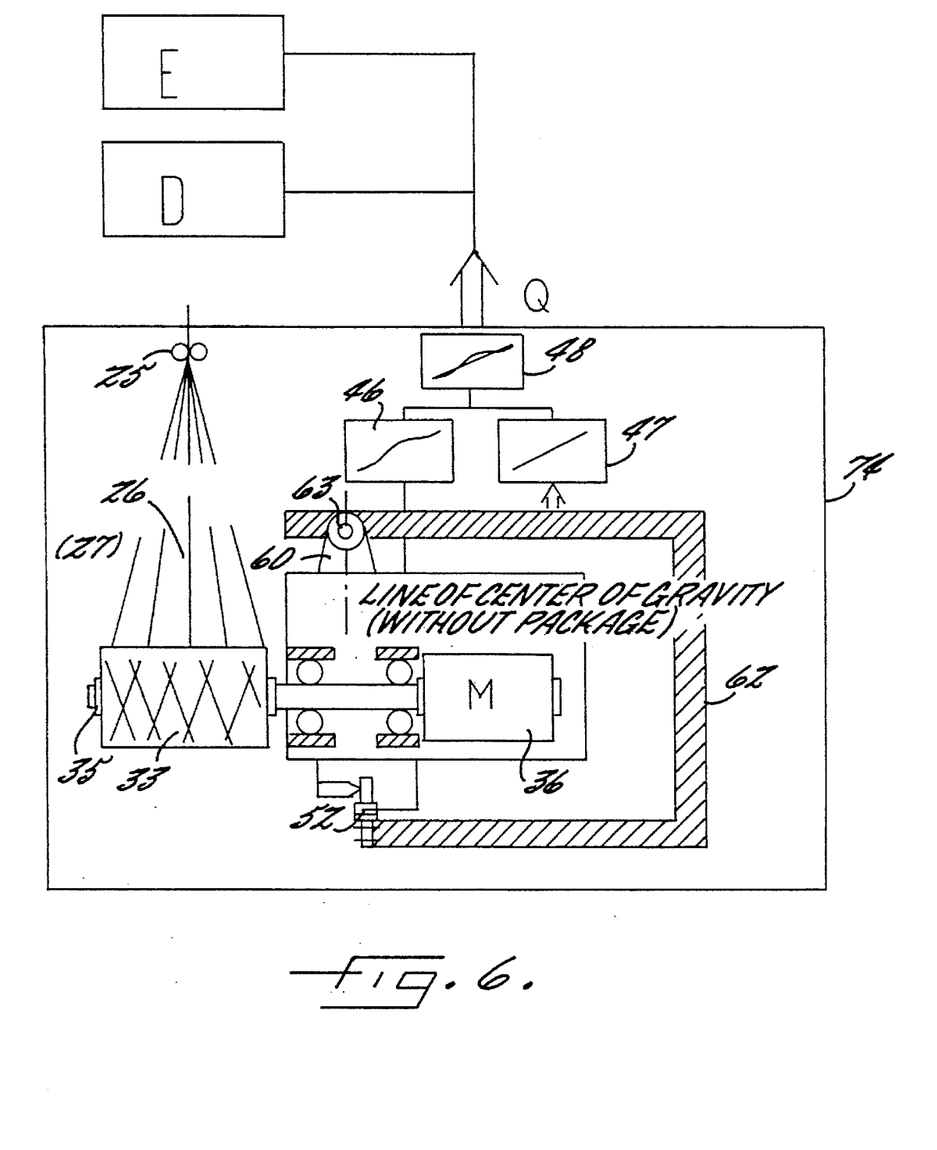
FIG. 6 shows a further embodiment of a winding head with a weight sensor.
Figure 7:
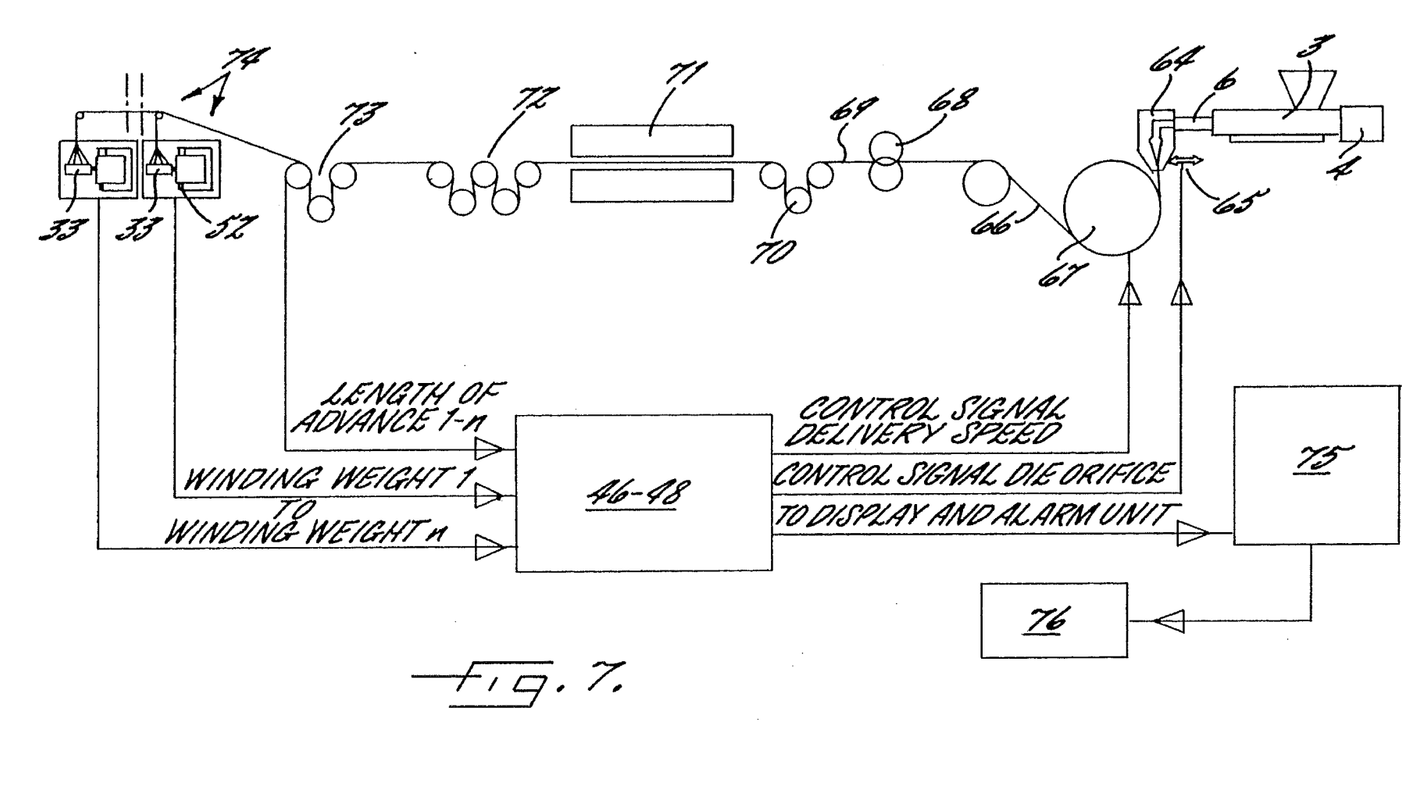
FIG. 7 is a schematic view of a slit-film production line with sensor winding heads and process control in accordance with the present invention.

FIG. 6 illustrates a winding head 74 of a spinning system or a slit film production line in accordance with FIG. 7, which is modified in comparison with FIG. 5. In this embodiment, the entire winding head 74, consisting of winding spindle 34, bearing and drive motor 36, as well as contact roll 28 and yarn traversing mechanism 27 is pivotally supported along the line of its center of gravity, i.e. a vertical line through the center of gravity of winding head 74 without package 33 held thereon. The pivot bearing 63 of swing support 60 is arranged in a frame structure 62 such that the torque caused by the forming package 33 loads weight sensor (weighing cell) 52 stationarily arranged on frame structure 62 with respect to axis of rotation 63 of pivot frame 62, which extends vertically to winding spindle 34. The evaluation of the weight signals supplied by weight sensor 52 occurs as in FIG. 5 and causes quality signals Q which are used to control the spinning and processing operations.

FIG. 7 is a schematic view of a system for producing slit films, for example, slit-film yarns for carpet backing, braids, binder twine, or the like. Also in this embodiment, the invention is realized with the use of takeup devices constructed as sensor winding heads 74 in accordance with FIG. 5 or FIG. 6, as is described below.

The thermoplastic material which is plasticized in extruder 3 by friction and additional heating, is extruded through melt line 6 and a subsequent wide slot-die 64 with orifice adjustment 65 to a flat film web, and withdrawn by a speed-adjustable cooling roll 67, and solidified by intensive cooling. Subsequently, the film web 66 passes through a cutting device 68, where it is split into a web of slit films 69. The latter is then drawn collectively through a first draw zone 70 with heat setting and a further draw zone 73, heat set and adjusted in its shrinkage. Finally, all slit films of web 69 are individually wound to cross-wound packages 33 on winding heads 74 with weight sensors in accordance with FIGS. 5 or 6.

The winding weights of packages 33, which are determined continuously or in timed fashion by the individual sensors 52 of winding heads 74 are input together with the length of advance of the slit-film web 69 as determined at delivery system 73 at the end of the shrinkage zone, into a central computer unit 46 and compared therein with the course of a representative desired value curve. The quality signals which are output by this unit, appear optically and, if need be, acoustically on a display and alarm unit 75, and trigger an alarm, when unacceptable deviations from the predetermined tolerance range occur. With a suitable programming of the evaluation unit, however, they are also output already when the tendency to such an unacceptable deviation becomes apparent, so as to warn the operating personnel as early as possible and to counteract these tendencies. However, the quality signals are also output as a graphic record on a printer 76 connected to display unit 75. Finally, the quality signals are used to control the process, namely to control the delivery speed of withdrawal by cooling roll 67, provided the signals of all package weight sensors 52 move in direction of an unacceptable deviation from the desired value or a predetermined tolerance range. However, when these signals fail to indicate a uniform tendency, but exhibit tendencies which possibly deviate in groups among each other, the quality signals will be used for adjustment 65 of the die orifice, so as to correct the thickness of the slit films in partial ranges of the extruded film web.

Figure 8:
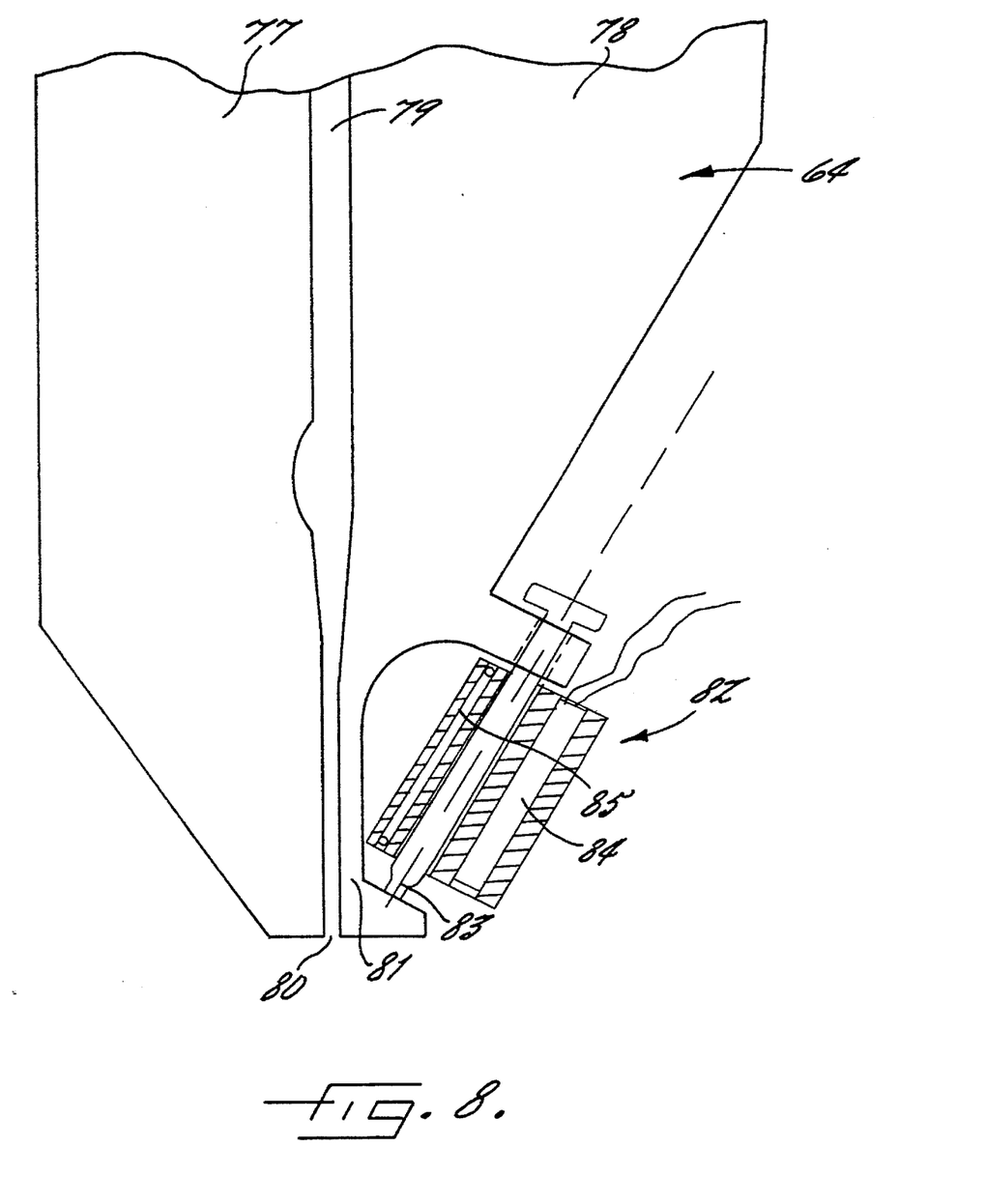
FIG. 8 is a schematic view of a wide-slot die with orifice adjustment.

Finally, shown in FIG. 8 is a wide-slot die 64 with an adjustment 65 of the die orifice, as is used in the extrusion line of FIG. 7. Such dies are known and commercially available. FIG. 8 shows the basic setup of such a flat film die 64. It consists of two halves 77 and 78, which form between them a melt duct 79 with a melt distribution over the width of die orifice 80. The one die half 77 is constructed substantially rigid, whereas the second die half 78 is provided with a flexible lip 81 as a result of a cross-sectional narrowing. This lip is divided, when viewed over its length, into several adjustment blocks which cooperate each with associated adjustment devices 82, and which are controlled by adjustment 65 of the die orifice as a function of determined quality signals.

The adjustment devices 82 consist of expansion pins 83 which are unilaterally held in second die half 78 and supported with their free end on the adjustment blocks of lip 81. The expansion pins 83 may be heated by heating cartridges 84 and are thereby lengthened, they may be cooled by cooling bores 85 and are thereby shortened, so that the length of the expansion pins is thermally changed, as need arises. As a result, force is introduced to die lip 81 in sections such as the die orifice adjustment requires it for this associated section. It should further be noted that this adjustment can be only a finest adjustment of die orifice 80 in a range from few 1/100 mm up to several 1/10 mm, whereas a manual coarse adjustment must previously be made by the operating personnel at the startup of the line. The described measures and the control of the line by determined quality signals allow to provide for a substantially automated operation with simultaneous product monitoring and quality control.

That which is claimed is:

1. A method of processing a continuous thermoplastic material while monitoring its quality, and comprising the steps of advancing the continuous thermoplastic material along a path of travel, winding the advancing thermoplastic material into a package, monitoring the weight and diameter of the package while it is being wound so as to permit the calculation of the density of the package, and including generating a control signal which is a function of the monitored weight, comparing the control signal with a predetermined reference signal, and generating an output signal at least during periods when the difference between the control signal and the reference signal exceeds a predetermined deviation, and such that the output signal represents the quality of the continuous material in the wound package.

2. The method as defined in claim 1 comprising the further step of applying a liquid finish to the advancing continuous material before it is wound into a package, and wherein the monitoring step includes monitoring the weight of the package and the weight of the liquid finish applied to the advancing material.

3. The method as defined in claim 2 wherein the step of monitoring the weight of the liquid finish applied to the advancing material includes measuring the weight of the advancing material per unit of time, and subtracting the weight of the package per unit of time so that the difference equals the weight of the applied liquid finish per unit of time.

4. The method as defined in claim 1 wherein the monitoring step is conducted continuously over the course of the winding step, and wherein the comparing step includes continuously comparing the control signal with a predetermined reference signal.

5. The method as defined in claim 1 wherein the monitoring step is conducted periodically over the course of the winding step, and wherein the comparing step includes periodically comparing the control signal with a predetermined reference signal.

6. The method as defined in claim 1 wherein the monitoring step is conducted at the beginning and at the end of a predetermined time interval during the course of the winding step, and wherein the comparing step includes comparing the change in the control signal during such time interval with a predetermined reference signal.

7. The method as defined in claim 1 wherein the monitoring step includes monitoring the increase of the control signal over the course of the winding step, or over the course of a predetermined portion of the course of the winding step, and wherein the comparing step includes comparing the monitored increase with a predetermined reference signal.

8. The method as defined in claim 1 wherein the monitoring step includes determining a time function derivative of the control signal, and wherein the comparing step includes comparing the time function derivative with a predetermined reference signal.

9. The method as defined in claim 1 wherein the monitoring step includes monitoring the weight of the package and the length of the continuous material advancing to the package, so as to permit the calculation of the denier of the continuous material advancing to the package.

10. The method as defined in claim 1 wherein the winding step includes winding the advancing material into the package which is supported on a cantilevered spindle, and with the spindle being rotatably supported by a spindle bearing, and wherein the monitoring step includes determining the weight of the package by monitoring the deflection of the spindle or the spindle bearing.

11. The method as defined in claim 1 wherein the winding step includes providing a winding apparatus which includes a spindle for supporting the package, a contact roll for engaging the package, and drive means for rotating the spindle and the contact roll, and wherein the monitoring step includes measuring the weight of the winding apparatus.

12. A method of processing a continuous thermoplastic material while monitoring its quality, and comprising the steps of advancing the continuous thermoplastic material along a path of travel, winding the advancing thermoplastic material into a package, monitoring continuously the diameter of the package while it is being wound, continuously calculating the square of the measured diameter, and continuously calculating the time derivative of the square of the measured diameter, generating a control signal which is a function of said time derivative, comparing the control signal with a predetermined reference signal, and generating an output signal at least during periods when the difference between the control signal and the reference signal exceeds a predetermined deviation, and such that the output signal represents the quality of the continuous material in the wound package.

13. A method of processing a continuous thermoplastic material while monitoring its quality, and comprising the steps of advancing the continuous thermoplastic material along a path of travel, winding the advancing thermoplastic material into a package, measuring the surface speed and the rotational speed of the package, so as to permit the package diameter to be calculated generating a control signal which is a function of the diameter, comparing the control signal with a predetermined reference signal, and generating an output signal at least during periods when the difference between the control signal and the reference signal exceeds a predetermined deviation, and such that the output signal represents the quality of the continuous material in the wound package.

14. The method as defined in claim 13 wherein the step of measuring the surface speed of the package includes contacting the surface of the package with a freely rotatable roller and measuring the rotational speed of the roller.

15. The method as defined in claim 13 including the further step of monitoring the weight and diameter of the package so as to permit the calculation of the density of the package.

16. A method of producing a plurality of strands of continuous thermoplastic material while monitoring the quality of each strand, and comprising the steps of extruding a thermoplastic material so as to form a plurality of separate strands, advancing each of the strands along a separate path of travel, winding each of the strands into a separate package, monitoring a physical parameter of each of the packages while it is being wound, and including generating a control signal for each of the packages which is a function of the monitored physical parameter, calculating the mean value of the control signals, comparing the control signal of each of the packages with the mean value, and generating an output signal at least during periods when the difference between the control signal and the mean value for a package exceeds a predetermined deviation, and such that the output signal represents the quality of the strand of thermoplastic material in the associated wound package.

17. The method as defined in claim 16 wherein the extruding step includes passing the thermoplastic material through a spinneret and wherein the winding step directly withdraws said strands from said spinneret.

18. The method as defined in claim 16 wherein the extruding step includes passing the thermoplastic material through a spinneret and wherein said strands are withdrawn from the spinneret by godets, the last of which advances said strands to an apex yarn guide and into a traversing triangle.

19. A method of producing a continuous thermoplastic material while monitoring its quality, and comprising the steps of extruding a thermoplastic material from an extruder so as to form a molten thermoplastic material which advances continuously along a path of travel, passing the molten advancing material through a die which comprises a slot-like opening, cooling the advancing material after having passed through the die so as to solidify the material, winding the solidified advancing material into a package, monitoring a physical parameter of the package while it is being wound, and including generating a control signal which is a function of the physical parameter, comparing the control signal with a predetermined reference signal, and generating an output signal at least during periods when the difference between the control signal and the reference signal exceeds a predetermined deviation, and such that the output signal represents the quality of the continuous material in the wound package, and wherein the step of generating said output signal includes controlling the width of the slot-like opening as a function of the output signal.

20. The method as defined in claim 19 wherein the step of generating an output signal includes terminating the method steps upon the output signal exceeding a predetermined value.

21. The method as defined in claim 19 wherein the step of generating said output signal includes controlling at least one of the method steps upon the output signal exceeding a predetermined level in a manner calculated to return the output signal to a value below said predetermined level.

22. The method as defined in claim 19 wherein the step of generating an output signal includes controlling the delivery rate of the advancing material from the extruder as a function of the output signal.

23. The method as defined in claim 19 wherein the step of extruding the material from said extruder includes heating the material, and the step of generating an output signal includes controlling the heat delivered to the material as a function of the output signal.

24. The method as defined in claim 19 wherein the step of generating an output signal includes controlling the cooling step as a function of the output signal.

25. The method as defined in claim 19 comprising the further step of slitting the advancing material upon exiting the slot-like opening to form a plurality of individual tapes of the material.

26. A winding apparatus for winding a continuously advancing strand of material into a package and comprising a rotatable winding spindle for supporting the package being formed thereon, said winding spindle being mounted in cantilevered fashion by means of a resiliently mounted bearing, and means operatively connected to said winding spindle for continuously measuring the weight of the package being formed thereon and including means for monitoring the deflection of said bearing caused by the weight of the package being formed thereon.

27. A method of processing a continuous thermoplastic material while monitoring its quality, and comprising the steps of advancing the continuous thermoplastic material along a path of travel, winding the advancing thermoplastic material into a package, monitoring the weight of the package and the length of the continuous material advancing to the package while it is being wound, so as to permit the calculation of the denier of the continuous material advancing to the package, and including generating a control signal which is a function of the weight, comparing the control signal with a predetermined reference signal, and generating an output signal at least during periods when the difference between the control signal and the reference signal exceeds a predetermined deviation, and such that the output signal represents the quality of the continuous material in the wound package.

28. A method of processing a continuous thermoplastic material while monitoring its quality, and comprising the steps of advancing the continuous thermoplastic material along a path of travel, winding the advancing thermoplastic material into a package, monitoring the weight of the package while it is being wound, and including generating a control signal which is a function of the weight, comparing the control signal with a predetermined reference signal, and generating an output signal at least during periods when the difference between the control signal and the reference signal exceeds a predetermined deviation, and such that the output signal represents the quality of the continuous material in the wound package, applying a liquid finish to the advancing continuous material before it is wound into the package, and wherein the monitoring step includes monitoring the weight of the package and the weight of the liquid finish applied to the advancing material, and wherein the step of monitoring the weight of the liquid finish applied to the advancing material includes measuring the weight of the advancing material before the liquid finish application per unit of time, and subtracting the measured weight of the advancing material before the liquid finish application per unit of time from the weight of the package per unit of time so that the difference equals the weight of the applied liquid finish per unit of time.

29. A winding apparatus for winding a continuously advancing strand of material into a package and comprising a rotatable winding spindle for supporting the package being formed thereon, said spindle being rotatably mounted to a frame structure, and said frame structure being pivotally mounted for movement about a transverse axis such that the weight of the package being formed on the spindle causes the frame structure to pivot in a predetermined direction about said axis, and means operatively connected to said winding spindle for continuously measuring the weight of the package being formed thereon and including means for monitoring the pivotal movement of said frame structure.

30. The winding apparatus as defined in claim 29 wherein said transverse axis passes through a vertical line which corresponds to the center of gravity of said frame structure and said spindle without said package being supported thereon.

31. The winding apparatus as defined in claim 29 wherein said frame structure includes biasing means for biasing the frame structure for pivotal movement about said axis in a direction opposite said predetermined direction.

* * * * *